United States Patent [19]

Fagerhol et al.

[11] Patent Number: 4,833,074

[45] Date of Patent: May 23, 1989

[54] PURIFIED HUMAN GRANYLOCYTE L1 PROTEINS METHODS FOR THEIR PREPARATION, MONOSPECIFIC ANTIBODIES AND TEST KITS

[75] Inventors: Magne K. Fagerhol; Inge Dale; Inger Naesgaard, all of Oslo, Norway

[73] Assignee: Ciba-Geigy Corporation, Ardsley, N.Y.

[21] Appl. No.: 117,429

[22] Filed: Nov. 2, 1987

Related U.S. Application Data

[63] Continuation of Ser. No. 628,061, Jul. 5, 1984, abandoned.

[30] Foreign Application Priority Data

Jul. 11, 1983 [GB] United Kingdom ................ 8318754

[51] Int. Cl.$^4$ .......................................... G01N 33/53
[52] U.S. Cl. ..................................... 435/7; 435/803; 435/810; 436/501; 436/518; 436/533; 436/536; 436/543; 436/547; 436/808; 530/350; 530/380; 530/412; 530/806; 530/827

[58] Field of Search ...................... 422/61; 424/85, 88; 435/7, 803, 810; 436/507, 518, 533, 543, 547, 808, 536; 530/350, 380, 412, 806, 827; 210/656, 660

[56] References Cited

PUBLICATIONS

Fagerhol et al., Scand. J. Haematol. 24, 393–398 (1980).
Fagerhol et al., Bull. Europ. Physiopath. Resp. 16 (suppl.), 273–281 (1980).
Willard et al., Clin. Chem., 28 1067–1073 (1982).
Dale et al., Eur. J. Biochem. 134 1–6 (1983).

*Primary Examiner*—Robert J. Warden
*Assistant Examiner*—Stephen C. Wieder
*Attorney, Agent, or Firm*—Irving N. Feit; JoAnn Villamizar

[57] ABSTRACT

The invention concerns the two pure human granulocyte L1 proteins of pI 6.3 and pI 6.5, and mixtures thereof, methods for their isolation and purification, their use as marker proteins and antigenics, antisera produced against these proteins, methods for producing said antisera, the use of said antisera for the qualitative and quantitative determinatoin of L1 proteins, and test kits comprising said antisera.

15 Claims, 2 Drawing Sheets

A  B  C

PURIFIED HUMAN GRANYLOCYTE L1 PROTEINS METHODS FOR THEIR PREPARATION, MONOSPECIFIC ANTIBODIES AND TEST KITS

This application is a continuation, of application Ser. No. 628,061, filed 7/5/84, abandoned.

FIELD OF THE INVENTION

The invention concerns two pure human granulocyte proteins, methods for their isolation and purification, their use, antisera produced against these proteins, methods for producing said antisera, the use of said antisera, and test kits comprising said antisera.

BACKGROUND OF THE INVENTION

Of the blood cells only the white blood cells, the leukocytes, have nuclei and are able to produce the many proteins found in blood plasma. One mm$^3$ of blood contains about 6 000 to 10 000 leukocytes. A subgroup of leukocytes are the granulocytes which again are subdivided into neutrophilic polymorph-nuclear granulocytes, which account for about 95% of all granulocytes, eosinophilic granulocytes and basophilic granulocytes. In healthy adults about $10^{11}$ granulocytes are released daily from the bone marrow, but this can be increased ten fold during severe infections and inflammatory conditions. Normally the leukocytes have a transit time of about 6 hours in the circulation before entering the tissues where they perform their biological functions and are eventually sequestered. Turnover of leukocytes may vary considerably in health and disease as shown by studies using isotope labelled granulocytes as well as histological methods showing varying degrees of leukocyte infiltration in tissues. However, none of these methods is readily available for clinical studies on the turnover of leukocytes. An alternative and more readily available method may be to monitor the release of one or more characteristic leukocyte proteins during the function and/or the sequestration of the leukocytes.

DESCRIPTION OF PRIOR ART

In three previous publications findings have been made suggesting that leukocytes contain a number of proteins that may vary in concentration during different diseases. Some of these proteins have been labeled L1, especially pI 6.3 and pI 6.5 L1 (reference 1 and 2) or R:6 and R:7 (reference 3). According to two-dimensional electrophoretic analysis (ISO-DALT) the pI 6.5 L1 protein is identical with the R:6 protein and the pI 6.3 L1 protein is identical with the R:7 protein. In publications (1) to (3) the proteins were seen on analytical methods among hundreds to thousands of other proteins. In publication (1) attempts were made to purify the L1-proteins with the purpose of establishing quantitative methods and preliminary characterisations. Preparative gel filtration, isoelectric focussing and affinity chromatography gave a protein with a molecular weight of about 51 000 Daltons (according to SDS polyacrylamide gel electrophoresis and gel filtration), which was very unstable, but which could be used for immunization of rabbits (1). The isolation and purification methods applied in reference (1) gave only very low yields of the 51 000 Dalton protein and often the protein was lost during the procedures. Immunization of rabbits by injecting the 51 000 Dalton protein gave an antiserum to the L1 proteins but often antibodies against other proteins as well. These antisera had to be freed from unwanted antibodies by adsorption with normal human serum or human tissue extracts. In publication (1) unfractionated leukocytes were extracted by freezing/thawing and mechanical homogenization of the leukocytes without addition of any enzyme inhibitors.

In publication (3) merely analytical methods for the determination of the R:6 and R:7 proteins are disclosed, however no isolation or purification procedures.

OBJECT OF THE INVENTION It is an object of this invention to establish gentle and efficient methods for extracting and purifying the L1 proteins from leukocytes to enable their characterization, and to prepare monospecific antisera or antibodies against these proteins. It is a further object of this invention to provide test kits comprising such antisera and/or such purified L1 proteins, optionally labelled with a radioactive isotope or with an enzyme which is suitable for quantitative assays of L1 proteins in body fluids or cell or tissue extracts.

SUMMARY OF THE INVENTION

Surprisingly it was found that the L1 proteins could be obtained in a pure and stable state if only granulocytes are used as source, and if the granulocytes are destroyed under such conditions that the lysosomes within the granulocytes are not simultaneously destroyed. This task is achieved by pressure homogenization of the granulocytes in the presence of an enzyme inhibitor and an agent that stabilizes the lysosomal membranes.

Accordingly, the invention concerns pure pI 6.3 and pI 6.5 L1 proteins and mixtures thereof, methods for their extraction from granulocytes by pressure homogenization of the granulocytes in the presence of an enzyme inhibitor and an agent that stabilizes the lysosomal membranes, and their purification by various methods, the use of said proteins for the preparation of monospecific antisera or antibodies, methods for producing said monospecific antisera or antibodies by immunization of experimental animals with said L1 proteins, the monospecific antisera and antibodies per se, the use of said antisera or antibodies and/or the purified L1 proteins for the qualitative and/or quantitative determination of the L1 proteins in cells, tissues and body fluids, and test kits comprising said pure L1 proteins, antisera and/or antibodies, optionally labeled by radioactive isotopes or by enzymes.

DETAILED DESCRIPTION OF THE INVENTION

Figure 1:
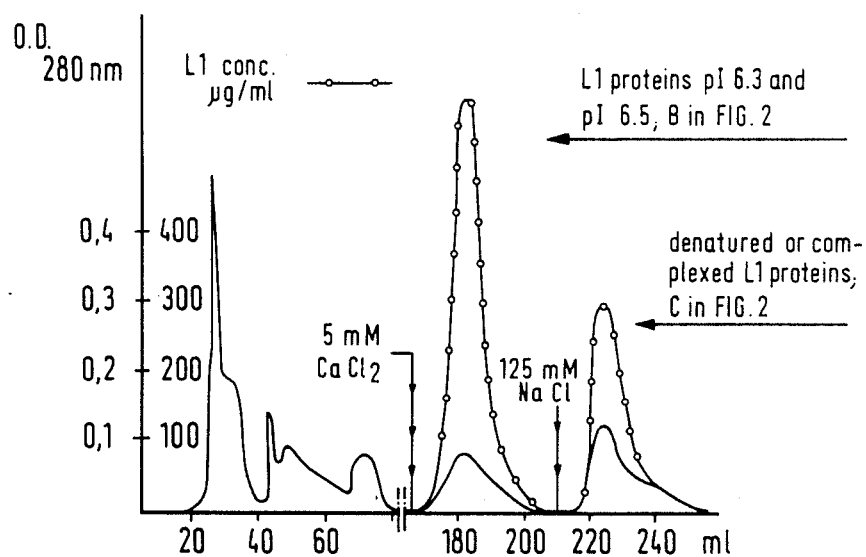

The invention in particular concerns the pure pI 6.3 and pI 6.5 L1 proteins, mixtures thereof and salts thereof.

Salts of the L1 proteins are especially non-toxic pharmaceutically acceptable salts or otherwise such which can be used for precipitation and/or purification processes of the L1 proteins.

Such salts are for example metal-salts, such as alkali metal or alkaline earth metal salts, e.g. sodium, potassium, magnesium, or calcium salts, or zinc salts, and the like, or ammonium salts with ammonia, or with primary, secunary or tertiary amines, for example salts with aliphatic, cycloaliphatic, cycloaliphatic-aliphatic or aralophatic primary, secondary or tertiary amines, such as with lower mono-, di- or tri-lower alkylamines, e.g. triethylamine, hydroxylower alkylamines, e.g. 2-hydroxyethylamine, bis-(2-hydroxy-ethyl) amine or° tris-(2-hydroxyethyl)amine, or with basic aliphatic esters of carboxylic acids, e.g. ethylenediaminetetraacetic acid lower alkyl esters, e.g. the tetraethyl ester, and the like.

Further salts are acid addition salts with inorganic acids, especially mineral acids, such hydrogene chloride, sulfuric acid, phosphoric acid, or with organic acids, such as carboxylic, sulfonic or sulfo acids, optionally substituted lower alkanecarboxylic acids, e.g. acetic acid, propionic acid, glycolic acid, maleic acid, hydroxmaleic acid, methylmaleic acid, malonic acid, fumaric acid, tartaric acid, citric acid, or optionally substituted aromatic acids, e.g. benzoic acid, cinnamic acid, mandelic acid, salicylic acid, 4-amino-salicylic acid, 2-phenoxybenzoic acid, 2-acetoxybenzoic acid, embonic acid, nicotinic acid, iso-nicotinic acid, or amino acids, lower alkanesulfonic acids, e.g. methane sulfonic acid, ethanesulfonic acid, 2-hydroxyethanesulfonic acid, benzenesulfonic acid, 4-methylbenzenesulfonic acid, naphthalinsulfonic acid, or ascorbic acid, and the like.

Both proteins are characterized by their isoelectric points at pH 6.3 and pH 6.5, respectively. The molecular weight of both proteins as determined by gel filtration and density gradient ultracentrifugation is the same and is about 36 500 Daltons. By SDS-electrophoresis on polyacrylamide gel the proteins are shown to consist of three polypeptides of about identical molecular weight of 12 500 Daltons. Each of those polypeptide chains has the following amino-acid sequence starting from the N-terminal: Met-Leu-Thr-Glu as shown by standard Deman procedure. The net electric charge and the availability of antigenic sites on the L1 proteins are greatly influenced by the absence or presence of calcium ions. The proteins will react much stronger as antigens in vitro in the presence of calcium ions.

The heat stability of the L1 proteins is high at neutral and alkaline pH. Boiling for 15 min in aqueous 5 mM EDTA, pH, 8.5 will retain 90% of the protein. The L1 proteins are partly precipitated by ethanol at acidic pH, e.g. of between about 4 and 5.

The L1 proteins have a characteristic distribution in the human body, being found in large amounts in neutrophilic granulocytes, monocytes, and squamous epithelium cells except normal skin. They are also found in many cancer cells of the squamous epithelial type and in some leukemia and lymphoma cells, especially those of the myelogenic leukemic type and monocytic lymphoma type. L1 proteins are found in the great majority of the squamous cancers of the urinary tract and lungs. The L1 proteins are also present in normal body fluids in relatively low concentrations in healthy individuals but in increasing concentrations in conditions with increasing degree of inflammation. In white blood cells the L1 proteins are present to 90% in the cytosol fraction.

The L1 proteins can be used as marker proteins, especially in radioactively labelled form, e.g. with $I^{125}$ or $P^{32}$, for the qualitative and/or quantitative determination of the L1 protein content in body fluids, cells and tissues.

The L1 proteins are good immunogens in animals, for example in rabbits.

The invention further concerns a method for the preparation of the pure pI 6.3 and pI 6.5 L1 proteins, mixtures thereof, and salts thereof, characterised in disrupting human granulocytes in a suitable buffer system, removing non-soluble cell material, and subjecting the supernatant to (a) isoelectric focussing and eluting the bands containing the pI 6.3 and/or the pI 6.5 L1 protein with a buffer, or (b) anion-exchange chromatography with an EDTA-containing buffer at a pH of about 8.5 and eluting the desired L1 proteins with a buffer containing calcium ions, or (c) affinity chromatography, or (d) preparative agarose gel electrophoresis, or (e) cation-exchange chromatography, or (f) gel filtration, or (g) reversible precipitation with $Zn^{++}$ or any combination of steps a) to g), freeing the eluates from any ampholytes and/or salts, concentrating the obtained solution of the pure L1 proteins, if desired, lyophilizing the obtained concentrated solution, and, if desired, transforming the obtained L1 proteins into a salt, or transforming the obtained salt into the free proteins.

The granulocytes used as source for the extraction of L1 proteins are obtained from fresh human blood by any conventional method, for example by dextran sedimentation and density gradient centrifugation.

The buffer system wherein the granulocytes are disrupted contains an agent preventing simultaneous disruption of the lysosomes, such as glycerol, dextrans, and preferably succrose, at a concentration sufficient to stabilize the osmotic pressure before and after the disruption of the cell walls. For example succrose is used at a concentration of between 0.27 and 0.34 M. The buffer system further contains enzyme inhibitors preventing digestion of the L1 proteins, such as diisopropylfluorophosphate (DFP), soybean trypsin inhibitor, Trasilol ®, mercury benzoate, pepstatin A, and preferably phenylmethylsulfonylfluorid (PMFS), and ethylenediaminetetraacetic acid (EDTA) or mixtures thereof.

The disruption of the cell wall can be performed in a conventional manner, for example mechanically, e.g. by a rotating mixer, a pestle (Potter-Elvelyem Method), by ultra sound, freezing and thawing, or combinations of these methods. In a preferred method the granulocytes are disrupted by pressure homogenization.

After disruption of the granulocytes insoluble materials, such as unbroken cells, cell debris and lysosomes, are removed, for example by ultracentrifugation.

The L1 proteins are obtained in pure form from the crude granulocyte extract by any of the following purification procedures.

(a) Isoelectric Focussing: The isoelectric focussing is performed preferably in a granulated gel, such as agarose or polymerized dextran beads containg a suitable mixture of commercially available ampholytes to provide a stable pH gradient of from about pH 5 to 8 during the procedure. This isoelectric focussing is performed with a maximum voltage of about 25 V/cm for about 10 to 20 hours at a temperature of about 5° to 15°. A preferred gel is Ultrodex ® and the preferred ampholyte is Ampholine ®.

The sample is preferably applied at the cathodical side of the gel.

Localisation of the L1 protein bands can be done by pH measurements along the gel surface or by staining filter paper prints of the top surface, for example with coomassie blue.

The bands containing the L1 proteins are scraped off, and eluted by a suitable buffer, containing EDTA at a pH of between about 7.5 and about 9, preferably at a pH of about 8.5.

The eluate is freed from the ampholytes and the salts by dialysis and/or gel filtration, and concentrated by ultrafiltration and/or lyophilisation.

(b) Anion Exchange Chromatography: The anion-exchange materials used in this method contain for example tertiary or quaternary amino groups, and are for example diethylaminoethyl cellulose, e.g. diethylaminoethyl Sepharose®, or QAE-cellulose (quaternary amino-ethyl cellulose). The granulocyte extract containing the L1 proteins is applied to the column in a low ionic strength buffer containing EDTA and with a pH of about 8.5. The L1 proteins are eluted specifically by a calcium ion containing buffer, for example a buffer containing 30 mM barbital and 5 mM calcium chloride.

(c) Affinity Chromatography: A third method of purifying the L1 protein is based on affinity chromatography. This can be performed on controlled pore glass beads having a large surface, e.g. of about 50 m$^2$/g. The glass beads are placed in a column and the crude granulocyte extract is applied in a suitable buffer of low molarity containing calcium ions at neutral or slightly acidic pH, e.g. of about pH 6 to 7. The L1 proteins are eluted with an alkaline buffer of about pH 7.5 to 8.5 containing about 50 mM EDTA and polyethylene glycol, or lithium bromide.

Another affinity chromatographic method makes use of an anti-L1 antibody column. The L1 proteins are adsorbed to the antibodies whereas other proteins are washed through with a buffer. Thereafter the L1 proteins are eluted with a salt solution, such as with an aqueous buffer of about pH 3.5 containing a salt, such as sodium chloride or sodium iodide.

(d) Preparative Agarose Gel Electrophoresis: Flat bed agarose gels of proper dimensions are used containing 75 mM barbital/2.5 mM EDTA buffer, pH 8.5. Electrophoresis is performed at 4 V/cm for 10–18 hours. The L1 protein bands are localized by staining of filter paper prints of the top gel surface. The L1 protein bands will be found in the $\alpha_2$-globulin region, and are eluted by freezing/thawing and centrifugation of the relevant strips of the agarose gel.

(e) Cation Exchange Chromatography: Cation exchange chromatography is performed on cation exchange resins, such as sulfopropyl substituted cellulose or polymerized dextran. The crude granulocyte extract is applied on the column after mixing with a low ionic strength buffer containing calcium ions and with a pH of about 6. Non-adsorbed proteins are washed away with the starting buffer and the L1 proteins are eluted with a buffer containing EDTA and increasing concentrations of sodium ions.

(f) Gel Filtration: For the gel filtration are used Sephadex® G75 to G200 agarose gels (Sepharose gels), such as Ultra gel® or polyacrylamide gel beads, such as Bio-Gel® P-60. The column preferably is a long one. The length of the column should be about 50 times of the diameter. The crude granulocyte extract is applied as such and the L1 proteins are chromatographed. For packing the column and processing is used a buffer preferably containing 0.1 M sodium citrate, 2.5 mM EDTA-K$_2$ and 0.25 mM thimerosal, pH 8.5. The L1 proteins will be found in a fraction corresponding to a molecular weight of 35 000 to 40 000 Daltons.

(g) Reversible Precipitation with $Zn^{++}$: The L1 proteins are quantitatively precipitated from aqueous solutions with neutral or alkaline pH by treatment with $Zn^{++}$-ions, especially in the form of water soluble zinc salts, such as zinc acetate or zinc chloride. For example an aqueous solution containing the L1 proteins can be treated at pH of about 8.5 with an about 10 mM to 100 mM aqueous solution of zinc acetate. The precipitated L1 zinc salt is collected, if necessary washed with the aqueous buffer solution, treated with a complexing acid, for example an about 100 mM aqueous dipotassium ethylenediaminetetraacetic acid solution of pH 8.5, and for recovering the free L1 proteins the solution is filtered through an ion exchange column, for example Pharmacia PD-10, and lyophilized.

Salts of the L1 protein are produced by conventional methods, e.g. by treatment with the relevant ions, e.g. a base, an acid, or a salt containing the desired ions or by ion exchange treatment. A very insoluble mangan salt can for example by prepared by adding $Mn^{++}$ions, for example in the form of an about 10 mM to 100 mM aqueous solution of manganese acetate or another water soluble manganese salt, to an aqueous solution of the L1 proteins.

The invention concerns also the monospecific antisera against the L1 protein and the antibody containing immunoglobulins, especially as produced by rabbits.

Monospecific antisera are produced by conventional methods, e.g. by weekly injection of the pure L1 proteins with complete Freund's adjuvant, e.g. subcutaneously or intramuscularly, in doses of about 100 µg per rabbit per week for about 8 to 16 weeks. Serum is then harvested from the animals e.g. by vene section, and clotting. Instead of rabbits also other non-human warm-blooded animals, especially mammals, e.g. sheep, goats, rats, mice, horses and the like may be used.

The monospecific antibody containing globulin fraction can be isolated from the serum by conventional methods, for instance by ion exchange chromatography.

For the production of said monospecific anti-L1 antibodies the monospecific antibody containing antiserum or the globulin fraction thereof is passed through a column where the purified L1-proteins have been conjugated to a suitable material, such as agarose or cellulose gel. After washing away the non-adsorbed proteins the anti-L1 antibody molecules are eluted by a buffer with a pH of about 3.5 containing sodium chloride or sodium iodide.

The relevant fractions are adjusted to a pH of about 7, dialysed and concentrated.

The anti-L1 antibodies, either purified or in crude form, such as in form of the antiserum or globulin fractions thereof, are used for the qualitative or quantitative methods for the detection of L1 proteins in cells, tissues or body fluids. Such methods include precipitation in gels, nephelometry, radio-immuno assay, enzyme immuno assay, immuno fluorescence and immuno peroxidase cytohisto-chemical techniques in conventional manners.

The invention further concerns test kits comprising the pure monospecific anti-L1 antibody, or the anti-L1 antibody globulin fraction, or the anti-L1 antibody containing antiserum. Such test kits are of conventional type and will be aimed at single radio-immuno diffusion, latex agglutination, spot test, radio-immuno assays, enzyme-immuno assays, immuno fluorescence or enzyme immuno-histochemical tests.

Such kits, in addition to anti-L1 antibodies in pure or crude form, dried or solubilized in a convenient buffer, may contain pre-made gels, latex, polystyrene, formalin stabilized animal red blood cells, or similar particles, enzymes, such as horse radish peroxidase, alkaline phosphatase, enzyme substrates, fluroescence or enzyme conjugated antibodies and materials suitable for separating antibody bound L1-molecules from free L1-molecules, such as killed strains of staphylococcus aureus belonging to the strains producing staphylococcus protein A, charcoal (which adsorbs the free L1-protein, but not the antibody-protein complex, or a second antibody, such as goat or antirabbit immunoglobulin, or L1-proteins labelled with radioactive isotopes, such as $J^{125}$, or with enzymes, such as with horse radish peroxidase or alkaline phosphatase. The kit may also contain carriers whereon monospecific anti-L1 antibodies are fixed to a surface, e.g. the internal surface of test tubes, surface of glass or plastic beads, pieces of filter paper, cellulose acetate membranes or similar materials, as well as buffers for such methods.

Hereinbefore and hereinafter the following abbreviations are used:
PMSF: phenylmethylsulfonylfluoride
PAGE: polyacrylamide gel electrophoresis
SDS: sodium dodecyl sulphate
IEF: isoelectric focussing
SRID: single radial immuno diffusion
NHS: normal human serum
ACD: acid-citrate-dextrose
DFP: diisopropylfluorophosphate
EDTA: ethylenediamine tetraacetic acid
EDTA-$K_2$: dipotassium salt of EDTA
DEAE: diethylaminoethyl
RIA: radio-immuno assay
PBS: phosphate buffered saline
PASA: protein A containing Staph. aureus Example 1: Isolation of granulocytes (a) A mixture consisting of 435 ml of fresh human blood, 65 ml of an aqueous solution containing 2.2% trisodium citrate dihydrate, 0.8% anhydrous citric acid and 2.45% dextrose, 250 ml high molecular weight dextran (Dextraven®-150) and 23 ml of a solution containing 2.5 mM citric acid, 45 mM trisodium citrate, 80 mM glucose and 15 mM sodium chloride is allowed to sediment for one hour at 4° C. The supernatant layer is harvested and centrifuged at 200×g for 20 min at 4° C. The sediment is treated with 50 ml of ice-cold distilled water whereby the red blood cells are lysed. After 30 sec isotonicity is restored by addition of 16.5 ml of ice-cold 0.6 M sodium chloride. The remaining leukocytes are washed twice with isotonic saline. The granulocytes are separated from the mononuclear cells by centrifugation on Lymphoprep® [density gradient centrifugation material consisting of 9.6% (w/v) of sodium metrizoate solution containing 5.6% (w/v) of an erythrocyte aggregating polysaccharide (Ficoll)] followed by centrifugation at 800×g for 20 min at 20° C. This procedure gives a yield of about $5 \times 10^8$ cells, about 95% thereof being granulocytes.

(b) Granulocyte Extraction

The cells obtained as described under a) are resuspended in 0.27 M succrose containing 10 mM PMSF, 2.5 mM EDTA-$K_2$, and 0.25 mM thimerosal, with Tris-buffer added to pH 8.5. Thereafter the cells are homogenized according to French and Holm (4) by exposure to 28 Kg/cm² of compressed air for two periods of 2 min while they are allowed to escape from the pressure chamber at a rate of one drop per second. During this procedure the cell containers were kept in wet ice. About 90% of the cells are disrupted and, after centrifugation at 100000×g for one hour, about 90% of the total L1 protein was found in the clear supernatant fluid. The latter will be referred to as the crude granulocyte extract. The total protein content is about 3 mg/ml, 30% of which are L1 proteins.

(c) Preparative Isoelectric Focussing (IEF)

For the preparative IEF 110×240×5 mm gel plates are used consisting of Ultradex® (Dextrane G75, refined) containing 2% (w/v) Ampholine® pH 5-8 (a mixture of synthetic ampholytes with buffering capacities at their isoelectric points). The samples [5 ml of the supernatant according to (b)]are mixed with an equal volume of Ultradex® gel and applied 5 cm from the cathode onto the gel plates. Separation is carried out for 18 hours with maximum 25 V cm$^{-1}$, 15 mA and 10 W. The protein bands are localized both by coomassie blue staining of a filter paper print of the gel plate and by pH measurements of the top gel surface. The L1 proteins in the pH 6.3 and 6.5 section are eluted with an equal volume of an aqueous solution containing 0.1 M sodium acetate, 2.5 mM EDTA-$K_2$, and 0.25 mM thimerosal, pH 8.5, by centrifugation at 2000×g for 20 min through 0.45 μm Millipore® filters. The ampholytes are removed by dialysis against the elution buffer over night. The remaining protein and buffer containing solutions are concentrated by ultrafiltration on Minicon® cells (semipermeable membrane). The yield of these procedures is about 20% of the L1 protein applied on the preparative IEF gel. 2.5 ml of this solution are applied on a Pharmacia® PD-10 column (Sephadex® G25 M) equilibrated with distilled water and the L1 proteins are eluted with 3.5 ml of distilled water and lyophilized to give 1 mg of pure L1 protein pI 6.3 and 6.5.

The pI 6.3 and the pI 6.5 L1 protein can also be purified separately by this method giving about 0.67 mg of the pI 6.5 and about 0.33 mg of the pI 6.3 L1 protein.

Example 2:

(a) The method takes advantage of the dramatic change in isoelectric point of the L1 protein when it is allowed to take up calcium ions (2). The protein, in crude granulocyte extracts, will bind to an anion exchanger, for instance of the diethylamonioethyltype, at alkaline pH and with a buffer containing ethylenediaminetetraacetic acid in sufficient amounts to bind calcium ions. The L1 proteins can subsequently be eluted specifically by adding calcium chloride to the buffer to ensure a final concentration of about 5-10 mM per liter.

Crude granulocyte extracts are prepared as described in Example 1. Their total protein contents are about 2-5 g per liter, of which about 60 per cent is L1 protein.

DEAE-Sephacel® (fron Pharmacia, Sweden) is equilibrated with 60 mM barbital buffer (7.7 g of diethylbarbituric acid and 10.5 g of the sodium salt thereof in 1 l of water) containing 1 g/l EDTA-$K_2$, pH 8.5, and packed on a chromatographic column with dimensin 1.5×5 cm, i.e. a volume of about 9 ml.

The sample, about 10 ml of crude granulocyte extract diluted with 30 ml of EDTA-$K_2$ barbital buffer pH 8.5 is applied with a peristaltic pump giving a flow rate of about 2 ml/min. Non-adsorbed proteins are washed out by 100 ml barbital buffer. Prior to elution of the L1 proteins the column is also washed with 30 ml of barbital buffer without EDTA-$K_2$. The L1 proteins are then eluted with 60 mM barbital buffer containing 5 mM CaCl$_2$, pH 8.5.

Figure 2:

FIG. 1 shows the total protein and L1 protein elution profile of such an ionexchange chromatography, and in FIG. 2 is shown the protein band patterns when crude leukocyte extract and purified L1 protein are subjected to analytical agarose gel electrophoresis. It can be seen that the purified L1 protein gives two major bands as described previously corresponding to pI 6.3 and pI 6.5.

The amount of L1 protein eluted with the calcium containing buffer is close to 50% of that applied in the sample and is found in a total volume of about 20 ml. This solution can conveniently be concentrated by ultrafiltration using Millipore ® CX-10 membranes. This leads to some loss of protein, depending upon whether or not EDTA is added to prevent L1 protein being bound to the membranes. Even without addition of EDTA an over all yield of about 35% can be achieved.

As shown in FIG. 1 some of the L1 protein is eluted with 60 mM barbital buffer containing 5 mM CaCl$_2$ and 125 mM NaCl, pH 8.5, but this protein gives bands mainly anodal and cathodal of the major L1 bands and may represent partly denatured or complexed L1 protein in addition to different proteins.

Large scale methods

The method described above can successfully be scaled up to handle 50 ml of crude granulocyte extracts. This is achieved by using a column containing about 50 ml DEAE-Sephacel ® (about 2.5×10 cm) and proportional increases in the volumes of the same buffers as given above.

(b) This takes advantage of the fact that a reversible precipitation of the L1 proteins can be obtained by addition of 10 mM Zn$^{++}$. To ten ml of crude leukocyte extract is added 90 ml of barbital buffer, 75 mM, pH 8.5, and 10 ml of a 100 mM Zn-acetate solution in water. The precipitate is washed several times, for instance five times, with 75 mM barbital buffer, pH 8.5, with 10 mM Zn-acetate. Finally the precipitate is washed with 75 mM barbital buffer, pH 8.5, and dissolved by dropwise addition of a solution of 100 mM EDTA-K$_2$ in water, pH adjusted to 8.5 by 5 M sodium hydroxide. This protein solution is applied on a Pharmacia PD-10 column equilibrated with distilled water and the L1 proteins are eluted with 3.5 ml of distilled water and lyophilized to give about 10 to 20 mg of pure L1 proteins.

Example 3: Preparation of Antiserum to purified L1

A solution containing about 1 mg/ml of pI 6.3 and pI 6.5 purified L1 protein (obtained according to Example 1 or 2) in 0.1 M sodium acetate, 2.5 mM EDTA, 0.25 mM thimerosal, pH 8.5, is homogenized with Freund's complete adjuvant. A volume of this mixture containing about 100 μg of L1 proteins is injected at multiple subcutaneous sites in rabbits once a week for six weeks. The rabbits are bled by vene puncture. The blood is allowed to clot at room temperature over night. Serum is harvested and tested for L1-antiserum activity.

Normally such antiserum can be used in dilution 1:32 for single radial immuno precipitation and in dilution 1:2000 for radio-immuno assay.

Example 4: Test Kit for Radio-immuno Assay

The test kit contains (for 100 tests):

| | |
|---|---|
| 1 ampoule | 2 ml lyophilized anti-L1 serum obtained according to Example 3 |
| 1 bottle | 100 ml RIA-buffer: 50 mM sodium chloride, 0.2% bovine serum albumin, 0.2% sodium azide adjusted to pH 7.4 |
| 1 rubber covered ampoule | 5 ml of aqueous solution of radioactive iodine$^{125}$ labeled L1-proteins adjusted to giving 500 cpm/ml (by the Bolton-Hunter method labeled) |
| 1 bottle | 100 ml of an aqueous suspension of formalin treated Staphylococcus aureus (PASA = protein A-containing Staph. aureus of Cowan I strain) in phosphate buffered saline |
| 1 bottle | 2 ml of a RIA-buffer solution containing 500 ng of L1 protein (reference solution) |

Procedure for quantitation of L1 proteins by RIA.

A series of standards is prepared by twofold dilution of the supplied L1 reference solution down to 7.8 ng/ml with RIA-buffer. In a series of test tubes is pipetted 25 μl of patient plasma diluted 1:30 in RIA buffer or standard reference solution. To this is added 20 μl of anti-L1 serum and the mixtures are incubated at 37° C. for 30 min. Then 50 μl of the solution with the radioactively labeled L1-protein is added following by incubating at 37° C. for 1 hour. To each tube is then added 1 ml of suspended Staph. aureus suspension and centrifuged at 2 000×g for 10 min. The supernatant is aspirated and the radioactivity in the sediment is measured. The percentage of the radioactivity relative to the radioactivity added initially is plotted for the L1 reference standard dilutions so that the reference curve can be drawn. The values from the patient samples can be read from this curve.

Example 5: Test Kit for Nephelometric Determination of L1 Proteins in Solution

The test kit contains:

| | |
|---|---|
| 1 ampoule | 1.5 ml anti-L1 antibody solution in buffer of pH 7.5 (sodium acetate buffer containing 5 mM calcium chloride) with a titre of about 1:32 when tested by double immuno diffusion in agarose gel. |
| 1 bottle | 20 ml dilution buffer as above |
| 1 ampoule | 0.5 ml of a solution of L1 protein in a concentration of 400 μg/ml. |

Anti-L1 serum is diluted 1:15 with dilution buffer. Six standards of L1 protein (1:1 until 1:64) are made by twofold dilution of the standard L1 solution. Then 250 μl of antibody dilution and 10 μl sample or diluted L1-standard is mixed in nephelometer cuvettes and incubated for ten minutes at room temperature. The optical density is read from the nephelometer.

Example 6: Test Kit for Single Radial-immuno Diffusion Analysis for L1 Proteins in Solution The test kit contains:

| | |
|---|---|
| 1 or more | premade agarose gels containing 2% of evenly distributed anti-L1 antibody solution with a titre of about 1:32 when tested by double diffusion in gel, and 0.1 M sodium acetate, 5 mM calcium chloride, 0.25 mM thimerosal, pH 8.5. |
| 1 ampoule | 0.1 ml of L1 protein solution with a concentration of 300 μg/ml. |

The agarose gel is provided in a closed chamber to prevent drying out of the gel. The gel has 18 premade wells for application of 10 μl of the standard solutions and the samples to be tested.

Example 7: Test Kits for Latex Agglutination Assay for a Semiquantitation Determination of L1 Protein The test kit contains:

| | | |
|---|---|---|
| (a) 1 bottle 2 ml | of a suspension of latex particles of 50 μm diameter to which purified L1 protein has been fixed. | |
| (b) 1 bottle 2 ml | of a buffer solution of anti-L1 antibody which will agglutinate the above mentioned latex particles, with a titre of 1:3 to 1:4 | |
| (c) 1 bottle 0.5 ml | of a buffer solution of the L1 protein in a concentration of 50 μg/ml | |

1 drop of (a), (b) and the patient sample to be tested are mixed on a black slide and observed for agglutination for 5 minutes. Lack of agglutination signifies an L1 concentration of above 1000 ng/ml. In the positive control solutions (a), (b) and (c) are mixed and no agglutination should develop.

Example 8: Test Kits for the Spot Test

The test kit contains:

10 pieces of cellulose acetate 5×50 mm with 2 spots with a diameter of 4 mm of dried specific anti-L1 antibody located 10 and 30 mm from one end

| | |
|---|---|
| (a) 1 bottle | 2 ml of a buffer solution containing specific anti-L1 antibodies conjugated with horse radish peroxydase |
| (b) 1 bottle | 10 ml of an aqueous Trisbuffer/isotonic saline pH 7.4 solution containing 1 mg/ml of diaminobenzidine (DAB) |
| (c) 1 bottle | 1 ml of an aqueous buffer solution of L1 protein in a concentration of 50 μg/ml |

For testing one drop of the sample solution is applied onto the first spot and one drop of solution (c) onto the second spot. After ten minutes the test strip is washed in Trisbuffer/saline for 5 minutes. Thereafter one drop of solution (a) is applied onto each spot and left for 10 minutes at room temperature and the strip is washed again for 5 minutes in the Trisbuffer/saline. To 1 ml of solution (b) 5 μl of 30% hydrogenperoxide is added. One drop of this mixture is applied onto each spot. A distinct brown coloration occuring after three minutes indicates the presence of L1 proteins in the sample.

By serial dilution of the sample the test can be made semiquantitative.

Example 9: Test Kits for L1 Proteins by Enzyme Immuno Assay

The test kits contain:

1 mikrotiter tray with 5×10 wells made of plastic material, the interior surface of the bottom and lower part of the wells are coated with specific anti-L1 antibodies

| | |
|---|---|
| (a) 1 bottle | 2 ml of a buffer solution containing specific anti-L1 antibodies conjugated with horse radish peroxydase |
| (b) 1 bottle | 10 ml of an aqueous Trisbuffer/isotonic saline pH 7.4 solution containing 1 mg/ml of diaminobenzidine (DAB) |
| (c) 1 bottle | 1 ml of an aqueous buffer solution of L1 protein in a concentration of 50 μg/ml |

The test procedure: 50 μl of the test sample solution or of solution (c) are added to the wells and incubated at room temperature for one hour. The wells are then washed with Trisbuffer/saline containing 0.5% of bovine serum albumine. To each well is added 50 μl of solution a) and incubated for one hour at room temperature. The wells are washed as above. To 1 ml of solution (b) are added 5 μl of 30% hydrogen peroxide, and 50 μl of this mixture is added to each well. The tray is incubated for 30 min at room temperature and the colour intensity in each well is determined photometrically.

Legends to figures

FIG. 1: Chromatographic profile of 9 ml crude leukocyte extract on a DEAE-Sephacel® column, 1.5×5 cm. The total protein content was determined by UV light absorbance at 280 nm and the L1 concentration by single radial immunodiffusion.

FIG. 2: Protein band patterns of crude granulocyte extract (A), the 5 mM $CaCl_2$ fraction (B) and the 125 mM NaCl fraction (C) on agarose gel electrophoresis in barbital buffer, 75 mM, with 2.5 mM EDTA-$K_2$, pH 8.5. Fraction B contains the two pure L1 proteins pI 6.3 and pI 6.5.

Literature references:

(1) Magne K. Fagerhol, Inge Dale and Terje Andersson, Scand. J. Haematol. (1980) 24, 393–398

(2) M.K. Fagerhol, I. Dale, T. Andersson, Bull. europ. Physiopath. resp. 1980, 16 (suppl) 273–281.

(3) Karen E. Willard, Anne Karine Thorsrud, Eimar Munthe and Egil Jellum, Clin. Chem., Vol. 28, No. 4, 1067–1073 (1982)

(4) French, P.C. and Holm, R.A., (1974) Thromb. Diath. Haemorrh. 32, 432–440.

What is claimed is:

1. Purified pI 6.3 and pI 6.5 L1 proteins having a molecular weight of 36,500 daltons, and mixtures and salts thereof.

2. The purified pI 6.3 L1 protein and salts thereof according to claim 1.

3. The purified pI 6.5 L1 protein and salts thereof according to claim 1.

4. The proteins of claim 1 wherein said proteins are labeled for use as marker proteins.

5. A method for the preparation of pure pI 6.3 and PI 6.5 L1 proteins, mixtures thereof, and salts thereof, comprising disrupting human granulocytes under such conditions that the lysosomes within the granulocytes are not simultaneously destroyed, removing non-soluble cell material, and subjecting the supernatant to
   (a) isoelectric focussing and eluting the bands containing the pI 6.3 and/or the pI 6.5 L1 protein with a buffer, or
   (b) anion-exchange chromatography with an EDTA-containing buffer at a pH of about 8.5 and eluting the desired L1 proteins with a buffer containing calcium ions, or
   (c) affinity chromatography, or
   (d) preparative agarose gel electrophoresis, or
   (e) cation-exchange chromatography, or
   (f) gel filtration, or
   (g) reversible precipitation with $Zn^{++}$, or any combination of steps a) to g), freeing the eluates from any ampholytes and/or salts, concentrating the obtained solution of the pure L1 proteins, if desired, lyophilizing the obtained concentrated solution, and, if desired, transforming the obtained L1 proteins into a salt, or transforming the obtained salt into the free proteins.

6. The monospecific anti-L1 antisera and monospecific anti-L1 antibodies produced by pure L1 proteins of claim 1.

7. The monospecific anti-L1 antisera and antibodies according to claim 6 obtained from rabbits.

8. A test kit for the quantitative detection of L1 proteins comprising as individual componets a monospecific anti-L1 antibody, an anti-L1 antibody globulin fraction, or an anti-L1 antibody containing antiserum, and purified pI 6.3 or pI 6.5 L1 proteins having a molecular weight of 36,500 daltons suitably labelled for quantitative assays.

9. A test kit according to claim 8, comprising lyophilized anti-L1 serum, RIA-buffer, radioactive iodine 125 labeled L1-proteins, an aqueous suspension of formalin treated staphylococcus aureus in phosphate buffered saline and an RIA buffer containing L1 protein standard.

10. A test kit according to claim 8, comprising an anti-L1 antibody solution in buffer of pH 7.5, a dilution buffer of pH 7.5, a standardized solution of L1 protein.

11. A test kit according to claim 8, containing premade agarose gels containing an evenly distributed anti-L1 antibody and 0.1 sodium acetate, 5 mM calcium chloride and 0.25 mM thimerosal, pH 8.5, and standardized L1 protein solution.

12. A test kit according to claim 8, comprising a suspension of latex particles to which purified L1 protein has been fixed, a buffer solution of anti-L1 antibody, and a standardized buffer solution of L1 protein.

13. A test kit according to claim 8, comprising sheets of cellulose acetate, a buffer solution containing specific anti-L1 antibodies conjugated with horse radish peroxidase, aqueous Trisbuffer/isotonic saline pH 7.4 solution containing diaminobenzidine and a standardized aqueous buffer solution of L1 protein.

14. A test kit according to claim 8, comprising a microtiter tray with wells coated with specific anti-L1 antibodies, a buffer solution containing specific anti-L1 antibodies conjugated with horse radish peroxidase, an aqueous Trisbuffer/isotonic saline pH 7.4 solution containing diaminobenzidine and a satandardized aqueous buffer solution of L1 protein."

15. A method for qualitatively and quantitatively determining the presence and amount of L1 protein in body fluids, cells and tissues comprising binding monospecific antisera or antibodies according to claim 6 to the L1 protein and determining the presence and amount of the antibody-protein complex as an indication of the presence and amount of the L1 protein.

* * * * *